United States Patent
Yoshioka et al.

(10) Patent No.: US 9,291,620 B2
(45) Date of Patent: Mar. 22, 2016

(54) IN VITRO DIAGNOSTIC TOOL, MEMBRANE FOR IN VITRO DIAGNOSTIC TOOL, AND PRODUCTION METHODS OF THE TOOL AND THE MEMBRANE

(71) Applicant: Panasonic Intellectual Property Management Co., Ltd., Osaka (JP)

(72) Inventors: Yuki Yoshioka, Osaka (JP); Takahiro Kurokawa, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 14/414,702

(22) PCT Filed: Jan. 18, 2013

(86) PCT No.: PCT/JP2013/000223
§ 371 (c)(1),
(2) Date: Jan. 13, 2015

(87) PCT Pub. No.: WO2014/013635
PCT Pub. Date: Jan. 23, 2014

(65) Prior Publication Data
US 2015/0168395 A1    Jun. 18, 2015

(30) Foreign Application Priority Data
Jul. 19, 2012  (JP) ................. 2012-160972

(51) Int. Cl.
*G01N 21/75*   (2006.01)
*G01N 33/543*   (2006.01)
(Continued)

(52) U.S. Cl.
CPC .......... *G01N 33/54386* (2013.01); *B05D 1/007* (2013.01); *G01N 33/54346* (2013.01); *G01N 33/558* (2013.01)

(58) Field of Classification Search
CPC ................. G01N 33/54346; G01N 33/54386; G01N 33/558; B05D 1/007
See application file for complete search history.

(56) References Cited

U.S. PATENT DOCUMENTS 5,821,073 A   10/1998 Lee
2003/0209485 A1   11/2003 Kools
(Continued)

FOREIGN PATENT DOCUMENTS

EP   0806666 A2   11/1997
EP   1284811 A1   2/2003
(Continued)

OTHER PUBLICATIONS

International Search Report issued in International Application No. PCT/JP2013/000223 dated Apr. 23, 2013.

*Primary Examiner* — Dennis M White
(74) *Attorney, Agent, or Firm* — McDermott Will & Emery LLP (57) ABSTRACT

Provided is an in vitro diagnostic tool configured to quantitatively or qualitatively detect a suspected substance in a test solution, the tool including: a first porous layer having a first surface and a second surface; a base sheet bonded to the first surface; a second porous layer bonded to the second surface; and a reagent configured to react with the suspected substance and carried in at least a part of the second porous layer, wherein: the first porous layer has a matrix structure of first nanofibers formed by electrostatic spinning; the second porous layer has a matrix structure of second nanofibers formed by electrostatic spinning; and a fiber diameter of the second nanofibers is smaller than a fiber diameter of the first nanofibers.

14 Claims, 4 Drawing Sheets

(51) Int. Cl.
B05D 1/00 (2006.01)
*G01N 33/558* (2006.01)

(56) References Cited

U.S. PATENT DOCUMENTS

| | | |
|---|---|---|
| 2003/0209486 A1 | 11/2003 | Kools |
| 2003/0213744 A1 | 11/2003 | Kools et al. |
| 2003/0217965 A1 | 11/2003 | Kools |
| 2004/0084364 A1 | 5/2004 | Kools |
| 2005/0040100 A1 | 2/2005 | Kools |
| 2005/0247621 A1 | 11/2005 | Kools |
| 2006/0057350 A1 | 3/2006 | Ochi et al. |
| 2006/0086657 A1 | 4/2006 | Kools |
| 2006/0180543 A1 | 8/2006 | Kools |
| 2006/0180544 A1 | 8/2006 | Kools |
| 2007/0187319 A1 | 8/2007 | Kools et al. |
| 2007/0274862 A1 | 11/2007 | Harttig |
| 2008/0145843 A1 | 6/2008 | Song |
| 2009/0252948 A1 | 10/2009 | Kools |
| 2010/0032366 A1 | 2/2010 | Kools |
| 2010/0156002 A1 | 6/2010 | Kools et al. |
| 2010/0200493 A1 | 8/2010 | Kools |
| 2010/0243556 A1 | 9/2010 | Kools et al. |
| 2011/0000286 A1 | 1/2011 | Harttig |
| 2011/0183563 A1 | 7/2011 | Ochi et al. |
| 2011/0263456 A1 | 10/2011 | Harttig |

FOREIGN PATENT DOCUMENTS

| | | |
|---|---|---|
| EP | 1284812 A2 | 2/2003 |
| EP | 1410838 A1 | 4/2004 |
| EP | 1509314 A1 | 3/2005 |
| EP | 1564315 A1 | 8/2005 |
| EP | 1820018 A1 | 8/2007 |
| EP | 1834692 A1 | 9/2007 |
| EP | 1932581 A1 | 6/2008 |
| EP | 2092341 A1 | 8/2009 |
| EP | 2316559 A1 | 5/2011 |
| EP | 2324906 A1 | 5/2011 |
| JP | 10-010125 A | 1/1998 |
| JP | 2004-501236 A | 1/2004 |
| JP | 2007-033086 A | 2/2007 |
| JP | 2008-523356 A | 7/2008 |
| JP | 2008-268043 A | 11/2008 |
| JP | 2010-513856 A | 4/2010 |
| WO | 01/89672 A1 | 11/2001 |
| WO | 01/89673 A2 | 11/2001 |
| WO | 03/097219 A1 | 11/2003 |
| WO | 2004/038073 A1 | 5/2004 |
| WO | 2006/061189 A1 | 6/2006 |
| WO | 2008/075214 A1 | 6/2008 |

IN VITRO DIAGNOSTIC TOOL, MEMBRANE FOR IN VITRO DIAGNOSTIC TOOL, AND PRODUCTION METHODS OF THE TOOL AND THE MEMBRANE

RELATED APPLICATIONS

This application is the U.S. National Phase under 35 U.S.C. §371 of International Application No. PCT/JP2013/000223, filed on Jan. 18, 2013, which in turn claims the benefit of Japanese Application No. 2012-160972, filed on Jul. 19, 2012, the disclosures of which are incorporated by reference herein.

TECHNICAL FIELD

The present invention relates to the field of in vitro diagnostic tools including a porous material produced using an electrostatic spinning mechanism configured to produce nanofibers from a polymer-containing solution by electrostatic force.

BACKGROUND ART

In association with satisfactory home medical care and community medical care in recent years, there is an increasing demand for analytical tools with which highly accurate in vitro diagnostic tests can be easily and quickly conducted by a user who does not necessarily have to be an expert in clinical testing. For example, dry-type in vitro diagnostic tools (e.g., biosensor) as typified by those for immunochromatographic tests do not require preparation of a reagent, and can very easily quantitatively or qualitatively analyze a suspected substance in a test solution.

The foregoing in vitro diagnostic tools typically comprise: a porous material in sheet form in which a test solution flows; a base sheet which holds the porous material; and a reagent carried in a part of the porous material. Moreover, due to a simple operation of supplying a fluid such as blood or urine containing a suspected substance to a predetermined contact portion of the porous material, the suspected substance can be easily and quickly analyzed.

Most porous materials used in conventional in vitro diagnostic tools have been single-layer membranes. On the other hand, development has also been conducted for a porous material in which microporous membranes are stacked. For example, Patent Literature 1 proposes a method in which two or more polymeric solutions are applied almost at once to a web-like support to form a double-layer liquid film, followed by washing, thereby to form a multi-layer microporous membrane.

PRIOR ART

Patent Literature

[Patent Literature 1] WO 2001/089673 pamphlet

SUMMARY OF INVENTION

Technical Problem

However, when an in vitro diagnostic tool is produced from a porous material that is a single-layer membrane, since the pore size distribution in the porous material is nearly uniform throughout the porous material, it is difficult to design a structure of the porous material in accordance with the intended use of the in vitro diagnostic tool. For example, the flow rate of the test solution cannot be controlled in the thickness direction of the porous material, and it is also difficult to change the pore size distributions in the region for carrying a reagent and in the path for the test solution to flow through.

On the other hand, a conventional multi-layer membrane useable in an in vitro diagnostic tool is produced by forming a film from a polymeric solution and then making the film porous. In such a production method, it is difficult to individually control the pore size distribution per layer, and also to sufficiently increase the porosity of the porous material. Moreover, a flow path for a test solution extending continuously such that the film is penetrated, can be formed easily; whereas a flow path for a test solution extending continuously in a planar direction of the film, cannot be formed easily. Therefore, a conventional multi-layer membrane has been far from having a structure that suits a porous material for an in vitro diagnostic tool.

Solution to Problem

In view of the foregoing, one aspect of the present invention relates to an in vitro diagnostic tool configured to quantitatively or qualitatively detect a suspected substance in a test solution, the tool comprising:
a first porous layer having a first surface and a second surface,
a base sheet bonded to the first surface,
a second porous layer bonded to the second surface, and
a reagent configured to react with the suspected substance and carried in at least a part of the second porous layer,
the first porous layer having a matrix structure of first nanofibers formed by electrostatic spinning,
the second porous layer having a matrix structure of second nanofibers formed by electrostatic spinning, and
the fiber diameter of the second nanofibers being smaller than the fiber diameter of the first nanofibers.

Another aspect of the present invention relates to a membrane for an in vitro diagnostic tool configured to quantitatively or qualitatively detect a suspected substance in a test solution, the membrane comprising:
a first porous layer having a first surface and a second surface,
a base sheet bonded to the first surface, and
a second porous layer bonded to the second surface,
the first porous layer having a matrix structure of first nanofibers formed by electrostatic spinning,
the second porous layer having a matrix structure of second nanofibers formed by electrostatic spinning, and
the fiber diameter of the second nanofibers being smaller than the fiber diameter of the first nanofibers.

Still another aspect of the present invention relates to a production method of an in vitro diagnostic tool, the method comprising:
a step of preparing a base sheet,
a step of forming a first porous layer by depositing first nanofibers on one surface of the base sheet by electrostatic spinning,
a step of forming a second porous layer by depositing second nanofibers on a surface of the first porous layer not in contact with the base sheet, the fiber diameter of the second nanofibers being smaller than the fiber diameter of the first nanofibers, and
a step of causing a reagent configured to react with a suspected substance in a test solution, to be carried in at least a part of the second porous layer.

Yet another aspect of the present invention relates to a production method of a membrane for an in vitro diagnostic tool, the method comprising:

a step of preparing a base sheet, a step of forming a first porous layer by depositing first nanofibers on one surface of the base sheet by electrostatic spinning, and a step of forming a second porous layer by depositing second nanofibers on a surface of the first porous layer not in contact with the base sheet, the fiber diameter of the second nanofibers being smaller than the fiber diameter of the first nanofibers.

Advantageous Effect of Invention

According to the present invention, there can be obtained an in vitro diagnostic tool having a configuration suited for a test solution to flow therein and a suspected substance to be analyzed. Specifically, according to the in vitro diagnostic tool of the present invention, since the pore size distribution in the first porous layer and the pore size distribution in the second porous layer can each be individually controlled, a region suited for flowing of the test solution and a region suited for carrying of the reagent can be provided separately. Moreover, since the fiber diameter of the second nanofibers is smaller than the fiber diameter of the first nanofibers, the specific surface area of the second porous layer is relatively large; and therefore, the reagent can be carried in the second porous layer in required amounts and in a well dispersed manner. Alternatively, the fiber diameter of the first nanofibers can be made relatively large to reduce resistance against the flow of the test solution. Thus, the suspected substance can be quickly and highly accurately analyzed by the in vitro diagnostic tool.

While the novel features of the present invention are set forth particularly in the appended claims, the present invention, both as to organization and content, will be better understood and appreciated, along with other objects and features thereof, from the following detailed description taken in conjunction with the drawings.

BRIEF DESCRIPTION OF DRAWINGS

FIG. 1(*a*) is a schematic sectional view of the configuration of an in vitro diagnostic tool according to an embodiment of the present invention; and FIG. 1(*b*) is a schematic top view of the configuration of the in vitro diagnostic tool.

DESCRIPTION OF EMBODIMENT

An in vitro diagnostic tool of the present invention comprises: a first porous layer having a first surface and a second surface; a base sheet bonded to the first surface; a second porous layer bonded to the second surface; and a reagent configured to react with a suspected substance and carried in at least a part of the second porous layer. The first porous layer has a matrix structure of first nanofibers formed by electrostatic spinning, the second porous layer has a matrix structure of second nanofibers formed by electrostatic spinning, and the fiber diameter of the second nanofibers is smaller than the fiber diameter of the first nanofibers.

Hereafter, the combination of the first porous layer having the first surface and the second surface, the base sheet bonded to the first surface, and the second porous layer bonded to the second surface, will also be referred to as a membrane for an in vitro diagnostic tool.

Here, electrostatic spinning is a method in which electrostatic drawing (electrospinning) is used to form a porous material (non-woven fabric). Electrostatic drawing is a phenomenon in which a starting solution including a solvent and a solute such as polymeric resin dispersed or dissolved therein, is emitted or sprayed into a space; and the starting solution, electrostatically charged by application of electric charge thereto, is electrically stretched while in flight in the space, thereby to produce nanofibers. According to electrostatic drawing, nanofibers having a fiber diameter on a submicron scale or a nanoscale can be produced. The produced nanofibers are deposited on the base sheet or a collector to form a non-woven fabric.

The first porous layer and the second porous layer are both non-woven fabrics having pores or voids extending continuously in a three-dimensional manner. Therefore, in each of the layers, a flow path for a test solution extending continuously in the planar direction of the layer is formed, thus enabling smooth flow of the test solution in the planar direction of the layer. Moreover, since the respective non-woven fabrics have high porosity, the test solution can be quickly absorbed in larger amounts compared to when a microporous membrane is used (see Patent Literature 1).

In electrostatic spinning, the fiber diameter of the nanofibers varies depending on factors such as the state of the starting solution, the configuration of the jig that emits or sprays the starting solution into a space, and the intensity of the electric field in which electric charge is applied to the starting solution. Therefore, arbitrary selection of these conditions enables relatively easy control of the fiber diameter of the nanofibers.

Alternatively, an electrostatic spinning mechanism configured to produce nanofibers can be divided into a plurality of units, so that nanofibers of a different fiber diameter can be produced at each unit. In that case, the electrostatic spinning mechanism includes, for example: a first electrostatic spinning unit arranged upstream of the production line; and a second electrostatic spinning unit arranged downstream of the production line. Electrostatic spinning is conducted continuously by use of the first and second electrostatic spinning units, and a membrane for an in vitro diagnostic tool including the first and second porous layers can be formed without the necessity to conduct a complex process of bonding the first and second layers together. Here, the number of electrostatic spinning units is not particularly limited. If three or more electrostatic spinning units are used, it would be possible to obtain a membrane for an in vitro diagnostic tool having three or more porous layers.

In view of achieving a quick quantitative or qualitative analysis of the suspected substance, the flow rate of the test solution in the porous layer is preferably made as fast as possible; and to accelerate the flow rate of the test solution, the flow path for the test solution in the porous layer needs to be widened to reduce resistance in the path. However, to satisfy such requirement, the flow path for the test solution needs to be widened by increasing the fiber diameter in the porous layer. On the other hand, in view of improving the accuracy of the analysis of the suspected substance, the reagent configured to react with the suspected substance needs to be carried in a part of the porous layer in sufficient amounts and in a well dispersed manner. To satisfy such requirement, the specific surface area of the porous layer needs to be increased by making the fiber diameter smaller in the porous layer. Therefore, a region suited for flowing of the test solution and a region suited for carrying of the reagent are preferably provided in the in vitro diagnostic tool.

Since electrostatic spinning has the foregoing characteristics, it is easy to individually control the respective pore size distributions in the first porous layer and the second porous layer. Therefore, it becomes easier to produce an in vitro diagnostic tool having a region suited for flowing of the test solution and a region suited for carrying of the reagent.

In the in vitro diagnostic tool, the fiber diameter of the second nanofibers is smaller than the fiber diameter of the first nanofibers. Thus, the specific surface area of the second porous layer is larger compared to the specific surface area of the first porous layer. Therefore, the reagent can be carried in the second porous layer in required amounts and in a well dispersed manner. Thus, the accuracy of the analysis of the suspected substance by the in vitro diagnostic tool can be improved.

The fiber diameter of the second nanofibers is, for example, 100 to 400 nm and preferably 200 to 300 nm.

Since a matrix structure is formed using the second nanofibers with such fiber diameter, the specific surface area of the second porous layer becomes sufficiently large. Thus, the amount of the reagent to be carried can be increased and the dispersibility of the reagent can be improved. As a result, the sensitivity of the in vitro diagnostic tool becomes remarkably high, and an accurate analysis becomes possible even with a very small amount of the suspected substance.

Moreover, according to the in vitro diagnostic tool, the flow rate of the test solution in the first porous layer in its planar direction, and the flow rate of the test solution in the second porous layer in its planar direction, can be made different from each other. This enables easier control of distribution of the test solution flowing in the in vitro diagnostic tool.

For example, when the flow rate of the test solution in the second porous layer is faster than that in the first porous layer, the resistance against the flow of the test solution in the second porous layer is relatively small. Therefore, the distribution of the test solution in the thickness direction of the multi-layer membrane including the first and second porous layers, can be equalized. This is because, although the test solution tends to be distributed in larger amounts in the first porous layer that is closer to the base sheet due to gravity, the smaller resistance in the second porous layer than in the first porous layer enables the test solution to be distributed to the first porous layer side in a less concentrated manner.

However, depending on the intended use of the in vitro diagnostic tool, more importance may be placed on quickness of analysis from start to end, than equalization of the distribution of the test solution in the thickness direction of the multi-layer membrane. In that case, the flow rate of the test solution in the first porous layer in its planar direction is preferably greater (faster) than the flow rate of the test solution in the second porous layer in its planar direction. This is because the time required for the test solution to reach the region carrying the reagent can be shortened by accelerating the flow rate of the test solution in the first porous layer where the test solution tends to concentrate under the action of gravity.

In the in vitro diagnostic tool of the present invention, since the fiber diameter of the first nanofibers is larger compared to the fiber diameter of the second nanofibers, the structure of the first porous layer is relatively coarse, and the flow path through which the test solution passes tends to become wide. Therefore, it is relatively easy to reduce the resistance against the flow of the test solution in the first porous layer. Thus, it is also easy to make the flow rate of the test solution in the first porous layer in its planar direction, greater than the flow rate of the test solution in the second porous layer in its planar direction.

The fiber diameter of the first nanofibers is, for example, 500 to 900 nm and preferably 600 to 800 nm. Since a matrix structure is formed using the first nanofibers with such fiber diameter, the flow rate of the test solution in the first porous layer becomes faster, and the time required for analyzing the suspected substance can be made as short as possible. As a result, an in vitro diagnostic test can be conducted efficiently, thereby reducing the burden on the user of the in vitro diagnostic tool. Moreover, the fiber diameter of the first nanofibers is larger than the fiber diameter of the second nanofibers, but is smaller than the fiber diameter of a common non-woven fabric. Therefore, the first porous layer is also suited to have the region for carrying the reagent, and is considered second best to the second porous layer in terms of such suitability.

Here, the fiber diameter of the first nanofibers as well as the fiber diameter of the second nanofibers may be obtained, for example, as the average of the diameters of ten of the nanofibers arbitrarily selected, each of the diameters measured at an arbitrary portion of each of the ten nanofibers. Here, the diameter of the nanofiber corresponds to the diameter of the section of the nanofiber perpendicular to the length direction of the nanofiber. When such section of the nanofiber is not round, the maximum diameter of the nanofiber may be regarded as the diameter. The ratio of the fiber diameter D1 of the first nanofibers to the fiber diameter D2 of the second nanofibers: D1/D2 (where D1>D2) favorably suited for the in vitro diagnostic tool, is in the range of, for example, 2 to 4. However, the preferable range of the D1/D2 ratio may be changed as appropriate in accordance with the intended use of the in vitro diagnostic tool.

The membrane for an in vitro diagnostic tool of the present invention can be obtained by a production method comprising, for example: a step of preparing a base sheet; a step of forming a first porous layer by depositing first nanofibers on one surface of the base sheet by electrostatic spinning; and a step of forming a second porous layer by depositing second nanofibers on a surface of the first porous layer not in contact with the base sheet, the fiber diameter of the second nanofibers being smaller than the fiber diameter of the first nanofibers.

Moreover, the in vitro diagnostic tool of the present invention can be obtained by a production method that is the same as the foregoing production method of the membrane, except for further including a step of causing a reagent configured to react with a suspected substance, to be carried in at least a part of the second porous layer.

However, the production method of the in vitro diagnostic tool and the production method of the membrane for an in vitro diagnostic tool are not limited to the foregoing. For example, the second porous layer may be produced separately, instead of being deposited on the surface of the first porous layer; and the first porous layer and the second porous layer, each individually produced, may be bonded together in a later process.

The production method of the membrane for an in vitro diagnostic tool can be conducted by a production system in which, for example: the base sheet is conveyed from upstream to downstream of a production line; the first porous layer is formed on the primary surface of the base sheet conveyed; and subsequently, the second porous layer is formed on the surface of the first porous layer. Such production system comprises, for example: (i) a base sheet feeding machine configured to feed the base sheet to the production line; (ii) a porous layer forming machine having an electrostatic spinning mechanism configured to produce nanofibers from a starting solution by electrostatic force; and (iii) a collecting machine configured to reel in the membrane sent out from the porous layer forming machine.

In the electrostatic spinning mechanism of the porous layer forming machine, first nanofibers are produced at a position above the base sheet conveyed, and the first nanofibers produced are deposited on the primary surface of the base sheet to form a first porous layer; and subsequently, second nanofibers are produced at a position above the base sheet further conveyed, and the second nanofibers produced are deposited on the surface of the first porous layer to form a second porous layer.

The electrostatic spinning mechanism includes, for example: a first electrostatic spinning unit arranged upstream of the production line; and a second electrostatic spinning unit arranged downstream of the production line. Use of such electrostatic spinning mechanism enables efficient formation of a stacked body including two or more porous layers each having a different fiber diameter.

Note that "nanofibers" refer to a thread-like substance made of a polymeric material and having a fiber diameter of, for example, 10 to 800 nm and preferably 10 to 100 nm. The nanofibers may include various additives.

Examples of a polymeric material include: cellulose-based resins such as cellulose and nitrocellulose; biopolymers such as polylactic acid, polyglycolic acid, collagen, polyhydroxybutyrate, polyvinyl acetate, and polypeptide; fluorocarbon resins such as polyvinylidene fluoride (PVDF) and vinylidene fluoride-hexafluoropropylene copolymer; polycarbonate; polyarylate; polyester carbonate; polycaprolactone; polyamide; polyimide; polyamide-imide; polyacrylonitrile; polymethyl methacrylate; acrylonitrile-methacrylate copolymer; polyvinyl chloride; vinylidene chloride-acrylate copolymer; polyesters such as polyethylene terephthalate, polybutylene terephthalate, polyethylene naphthalate, poly-m-phenylene terephthalate, and poly-p-phenylene isophthalate; and resins such as polyethylene, polypropylene, polystyrene, and polyethylene oxide. These may be used singly or in a combination of two or more.

The starting solution for the nanofibers includes a solvent and a polymeric material dissolved therein. The solvent may be selected as appropriate in accordance with the polymeric material. Examples of the solvent include methanol, ethanol, 1-propanol, 2-propanol, hexafluoroisopropanol, tetraethylene glycol, triethylene glycol, dibenzyl alcohol, 1,3-dioxolane, 1,4-dioxane, methyl ethyl ketone, methyl isobutyl ketone, methyl n-hexyl ketone, methyl n-propyl ketone, diisopropyl ketone, diisobutyl ketone, acetone, hexafluoroacetone, phenol, formic acid, methyl formate, ethyl formate, propyl formate, methyl benzoate, ethyl benzoate, propyl benzoate, methyl acetate, ethyl acetate, propyl acetate, dimethyl phthalate, diethyl phthalate, dipropyl phthalate, methyl chloride, ethyl chloride, methylene chloride, chloroform, o-chlorotoluene, p-chlorotoluene, carbon tetrachloride, 1,1-dichloroethane, 1,2-dichloroethane, trichloroethane, dichloropropane, dibromoethane, dibromopropane, methyl bromide, ethyl bromide, propyl bromide, acetic acid, benzene, toluene, hexane, cyclohexane, cyclohexanone, cyclopentane, o-xylene, p-xylene, m-xylene, acetonitrile, tetrahydrofuran, N,N-dimethylformamide, N,N-dimethylacetamide, dimethyl sulfoxide, pyridine, and water. These may be used singly or in a combination of two or more.

An inorganic solid-state material may be added to the starting solution. Examples of the inorganic solid-state material include an oxide, a carbide, a nitride, a boride, a silicide, a fluoride, and a sulfide. Among these, an oxide is preferred in view of factors such as heat resistance of the nanofibers produced and processability thereof. Examples of an oxide include $Al_2O_3$, $SiO_2$, $TiO_2$, $Li_2O$, $Na_2O$, $MgO$, $CaO$, $SrO$, $BaO$, $B_2O_3$, $P_2O_5$, $SnO_2$, $ZrO_2$, $K_2O$, $Cs_2O$, $ZnO$, $Sb_2O_3$, $As_2O_3$, $CeO_2$, $V_2O_5$, $Cr_2O_3$, $MnO$, $Fe_2O_3$, $CoO$, $NiO$, $Y_2O_3$, $Lu_2O_3$, $Yb_2O_3$, $HfO_2$, and $Nb_2O_5$. These may be used singly or in a combination of two or more.

The mix ratio of the solvent and the polymeric material in the starting solution varies depending on the kind of solvent and the kind of polymeric material selected. The amount of the solvent in the starting solution is, for example, 60 mass % to 95 mass %.

Next, with reference to drawings, a description will be given of an example of the configuration of the in vitro diagnostic tool of the present invention.

Embodiment 1

Figure 1:
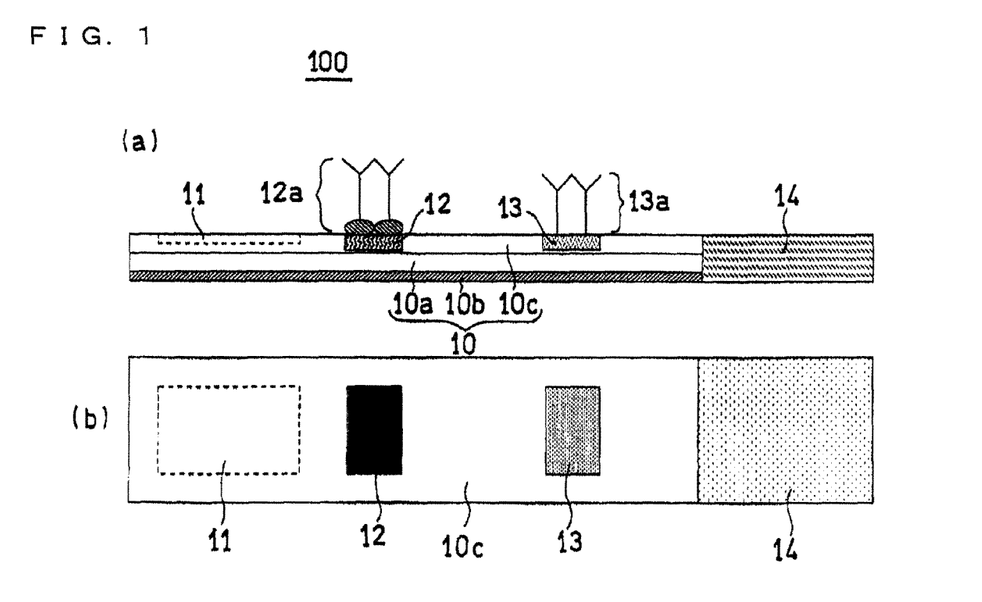

In FIG. 1, the configuration of an in vitro diagnostic tool according to an embodiment of the present invention is schematically illustrated. FIG. 1(a) is a sectional view of the in vitro diagnostic tool and FIG. 1(b) is a top view of the same.

Here, a description will be given of the case where an in vitro diagnostic tool 100 serves as an immunochromatographic test piece based on an antigen-antibody reaction.

The in vitro diagnostic tool 100 includes a membrane 10 therefor, i.e., a stacked body including: a first porous layer 10a having a first surface as the bottom planar surface and a second surface as the top planar surface; a base sheet 10b formed on the first surface of the first porous layer 10a; and a second porous layer 10c formed on the second surface of the first porous layer 10a. The first porous layer 10a and the second porous layer 10c are each formed of a non-woven fabric having a matrix structure of nanofibers formed by electrostatic spinning.

Figure 2:
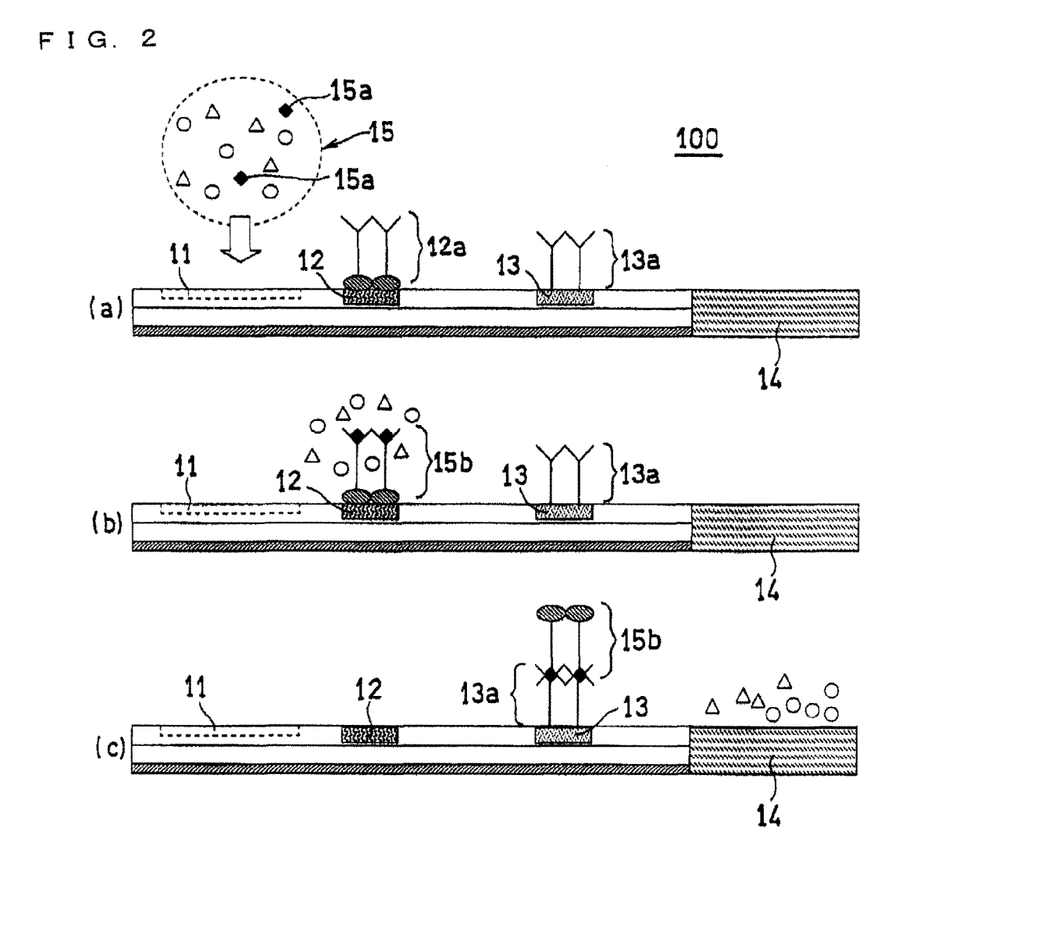
FIG. 2 is a schematic illustration depicting the principle for measuring a suspected substance using the in vitro diagnostic tool.

The shape of the membrane 10 for the in vitro diagnostic tool is not particularly limited, and is, for example, a rectangle as illustrated in FIG. 2. One short side portion of the rectangle serves as a test solution inlet portion 11 configured to introduce a test solution of, for example, blood, urine, or saliva into the membrane 10. The test solution inlet portion 11 is disposed at, for example, an open surface of the second porous layer 10c as illustrated in FIG. 1(a).

A first reagent holding portion 12 is disposed a short distance away from the test solution inlet portion 11 of the second porous layer 10c, and holds a labeling reagent 12a configured to specifically bind to a suspected substance (antigen) contained in the test solution that flows to the portion 12 due to osmosis. Moreover, a second reagent holding portion 13 is disposed farther away from the test solution inlet portion 11 of the second porous layer 10c and holds a detecting reagent 13a configured to immobilize a conjugate of the labeling reagent 12a and the suspected substance. Since the conjugate of the labeling reagent 12a and the suspected substance is immobilized by the detecting reagent 13a, the physical property of the second reagent holding portion 13 changes; and detection of this change enables quantitative or qualitative analysis of the suspected substance. Furthermore, at a position much farther away from the test solution inlet portion 11 than the second reagent holding portion 13, a solution absorbing portion 14 configured to collect the test solution and being contiguous to the membrane 10 of the in vitro diagnostic tool is provided.

Next, with reference to FIG. 2, a description will be given of the principle for detecting the suspected substance in the test solution using the in vitro diagnostic tool 100.

First, a few drops of a test solution 15 are dropped to the test solution inlet portion 11 of the in vitro diagnostic tool 100 (see FIG. 2 (a)). The test solution 15 dropped to the portion 11 is usually bodily fluid taken from a biological body and contains various substances. Here, a description will be given of the case where the bodily fluid contains an influenza A antigen 15a as the suspected substance.

The test solution 15 dropped into the test solution inlet portion 11 flows inside the first and second porous layers which are porous materials due to capillary action; and first, reaches the first reagent holding portion 12 where the labeling reagent 12a is held. The standard reagent 12a is carried in the second porous layer by a weak force, so that the labeling reagent 12a can easily dissolve from the first reagent holding portion 12. In the first reagent holding portion 12, only the influenza A antigen 15a specifically binds to the labeling reagent 12a to produce a conjugate 15b, as illustrated in FIG. 2(b). As the labeling reagent 12a, an anti-influenza A antibody labeled with colloidal gold or the like is used.

The conjugate 15b produced dissolves from the first reagent holding portion 12, flows toward the solution absorbing portion 14, and eventually reaches the second reagent holding portion 13 where the detecting reagent 13a is held. The detecting reagent 13a is firmly bound to the second porous layer and thus carried therein, so that the detecting reagent 13a does not dissolve from the second reagent holding portion 13. The detecting reagent 13a is, for example, an unlabeled anti-influenza A antibody. The conjugate 15b having the labeled anti-influenza A antibody is caught by the detecting reagent 13a, as illustrated in FIG. 2(c). As a result, the physical property of the second reagent holding portion 13 changes. Such change is indicated by, for example, a change in hue. The change in hue can be visually and thus easily observed by the tester. Substances in the test solution other than the conjugate 15b pass through the second reagent holding portion 13 and are collected by the solution absorbing portion 14.

Other than visual observation, the labeled anti-influenza A antibody present in the second reagent holding portion 13 can be detected by, for example, optical analysis using laser or electrochemical analysis.

The base sheet 10b is not particularly limited and can be, for example, a resin sheet, a paper sheet, a fabric sheet, or a glass fiber sheet, in strip form. The resin forming the resin sheet can be, for example, polyolefin, polyamide, polyimide, or polyester (e.g., polyethylene terephthalate, polybutylene terephthalate). The base sheet 10b may have a porous structure.

The first porous layer 10a has a matrix structure of first nanofibers formed by electrostatic spinning. When the intended use of the in vitro diagnostic tool is for an immunochromatographic test as illustrated in FIGS. 1 and 2, the fiber diameter of the first nanofibers is, for example, preferably 600 to 800 nm. Moreover, the thickness of the first porous layer 10a is, for example, preferably 10 to 150 μm. The material for the first nanofibers is, for example, preferably nitrocellulose.

The second porous layer 10c has a matrix structure of second nanofibers formed by electrostatic spinning. When the intended use of the in vitro diagnostic tool is for an immunochromatographic test, the fiber diameter of the second nanofibers is, for example, preferably 200 to 300 nm. The thickness of the second porous layer 10c is, for example, preferably 10 to 150 μm.

The solution absorbing portion 14 is not particularly limited as long as it is capable of collecting the test solution after completion of analysis, and may be a paper sheet or the like. Moreover, the material for the solution absorbing portion 14 may be the same as the one used for the base sheet, the first porous layer, or the second porous layer.

The labeling reagent 12a held in the first reagent holding portion 12 varies depending on the intended use of the in vitro diagnostic tool. As the labeling reagent 12a for an immunochromatographic test, a reagent based on an antibody configured to specifically bind to various antigenic substances contained in the test solution, is used. The labeling reagent 12a preferably has a label capable of making analysis easier. The labeled antibody can flow freely when not immobilized on the nanofibers; and tends to dissolve into the test solution, with an antigen bound thereto.

As with the labeling reagent 12a, the detecting reagent 13a held in the second reagent holding portion 13 is also selected in accordance with the intended use of the in vitro diagnostic tool. For example, a reagent based on the same antibody as the one used for the labeling reagent 12a is used. The antibody used as the detecting reagent 13a is immobilized on the second nanofibers at the second reagent holding portion 13. Thus, the antigen bound to the labeled antibody is caught by the detecting reagent 13a and immobilized at the second reagent holding portion 13. Therefore, the antigen can be quantitatively or qualitatively measured by the change in the physical property of the second reagent holding portion 13.

For example, when there is a change in hue of the second reagent holding portion 13, a specific antigen (suspected substance) is found to be contained in the test solution. Thus, it is possible to clarify at least a part of the properties of the test solution, based on the presence or absence of such change. Moreover, by referring to the degree of the change in the hue, it is possible to evaluate the concentration of the suspected substance contained in the test solution.

Next, a detailed description will be given of an example of the production method of the in vitro diagnostic tool.

First, a description will be given of the production method of the membrane for an in vitro diagnostic tool, the method comprising: (i) a step of preparing a base sheet; (ii) a step of forming a first porous layer by depositing first nanofibers on one surface of the base sheet, by electrostatic spinning; and (iii) a step of forming a second porous layer by depositing second nanofibers on a surface of the first porous layer not in contact with the base sheet, the fiber diameter of the second nanofibers being smaller than the fiber diameter of the first nanofibers.

The steps (i) to (iii) can be conducted as one continuous process in which, for example, the base sheet is conveyed from upstream to downstream of a production line, the first porous layer is formed on the primary surface of the base sheet conveyed, and subsequently, the second porous layer is formed on the surface of the first porous layer.

More specifically, in terms of efficiency, it is preferable to conduct on the production line, (i) a step of feeding a base sheet to a space for nanofiber formation; (ii) a step of producing first nanofibers from a starting solution by electrostatic force in the space for nanofiber formation, and forming a first porous layer by depositing the produced first nanofibers on the primary surface of the base sheet; (iii) a step of forming a second porous layer on the surface of the first porous layer, such that the second porous layer covers the first porous layer; and (iv) a step of collecting the completed membrane.

In the steps (ii) and (iii), the process from production of the nanofibers to formation of the porous layers is conducted using an electrostatic spinning mechanism. The electrostatic spinning mechanism includes, for example: a discharger comprising a container configured to contain the starting solution and provided with a discharge outlet configured to discharge the starting solution in a certain direction; an electrostatic charging means configured to electrostatically charge the starting solution discharged; and a collector configured to collect the nanofibers produced from the starting solution in the determined space. The collector is preferably configured to be in parallel with the base sheet, so that the nanofibers would be deposited on the base sheet conveyed. That is, the discharger is arranged at a position above the space for producing the nanofibers; the collector is arranged at a position below the space for producing the nanofibers; and the base sheet is conveyed in one direction along the collector.

In the electrostatic spinning mechanism, the starting solution discharged from the discharger moves into the determined space; and as the electrostatically charged starting solution flies in the space, the solvent gradually evaporates therefrom. This causes the volume of the starting solution in flight to gradually decrease. As a result, the electric charge density of the starting solution in flight in the space gradually increases. As the electric charge density of the starting solution becomes high, and once the Coulomb repulsive force in the starting solution becomes greater than the surface tension of the starting solution, there occurs a phenomenon in which the starting solution explosively stretches linearly. This phenomenon corresponds to electrostatic drawing. According to electrostatic drawing, it is possible to efficiently produce nanofibers having a fiber diameter of a size ranging from submicrons to the order of a nanometer.

The fiber diameter of the nanofibers produced varies depending on factors such as the state of the starting solution, the configuration of the discharger, and the intensity of the electric field generated by the electrostatic charging means. Therefore, the electrostatic spinning mechanism can be divided into a plurality of units, and nanofibers of a different kind can be produced at each unit. When the electrostatic spinning mechanism includes a first electrostatic spinning unit arranged upstream of the production line and a second electrostatic spinning unit arranged downstream of the production line, it is possible to successively form the first porous layer using the first electrostatic spinning unit and then the second porous layer having a fiber diameter smaller than the fiber diameter of the first nanofibers using the second electrostatic spinning unit.

Next, with reference to drawings, a description will be given of the production system and production method of the membrane for an in vitro diagnostic tool. However, the following system and method are not to be construed as limiting in any way the scope of the present invention.

Figure 3:
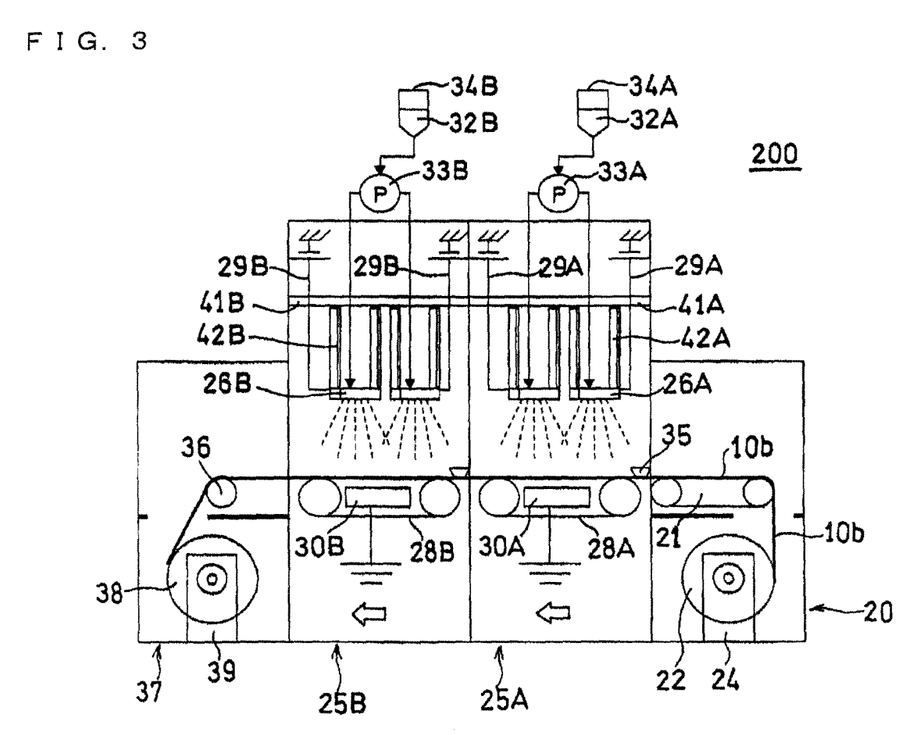
FIG. 3 is an illustration of the configuration of an example of a system for producing a membrane for an in vitro diagnostic tool.

FIG. 3 is a schematic illustration of the configuration of an example of the production system of the membrane for an in vitro diagnostic tool.

A production system 200 comprises a production line for producing a membrane for an in vitro diagnostic tool. In the production system 200, a base sheet is conveyed from upstream to downstream of the production line. On the base sheet being conveyed, a first porous layer and then a second porous layer are formed successively.

Provided on the most upstream side of the production system 200, is a base sheet feeding machine 20 which houses a base sheet 10b wound in roll form. The base sheet feeding machine 20 reels out the rolled base sheet 10b and feeds it to another machine adjacently arranged on the downstream side. Specifically, the base sheet feeding machine 20 causes a feeding reel 22 to rotate by a motor 24 and feeds the base sheet 10b wound on the feeding reel 22 to a first conveyor 21.

The base sheet 10b reeled out is moved to a first electrostatic spinning unit 25A and then to a second electrostatic spinning unit 25B, by the first conveyor 21. Electrostatic spinning mechanism of the first electrostatic spinning unit 25A and that of the second electrostatic spinning unit 25B include: a discharger 26A and a discharger 26B configured to discharge a starting solution, set at the upper parts of the units; electrostatic charging means configured to electrostatically charge the starting solution discharged; and a second conveyor 28A and a second conveyor 28B configured to convey the base sheet 10b from upstream to downstream, with the base sheet 10b facing the discharger 26A and the discharger 26B. The second conveyors 28A and 28B function as a collector in collaboration with the base sheet 10b to collect nanofibers.

The electrostatic charging means comprise: voltage applying devices 29A and 29B configured to apply voltage to the dischargers 26A and 26B; and counter electrodes 30A and 30B set in parallel with the second conveyors 28A and 28B. The counter electrodes 30A and 30B are grounded. By such grounding, an electric potential difference (e.g., 20 to 200 kV) corresponding to the voltage applied by the voltage applying devices 29A and 29B can be provided between the dischargers 26A and 26B and the counter electrodes 30A and 30B. Note that the respective configurations of the electrostatic charging means are not particularly limited, and for example, the counter electrodes 30A and 30B are not necessarily grounded. Moreover, as alternatives to providing the counter electrodes 30A and 30B, respective belt parts of the second conveyors 28A and 28B may be formed from a conductive matter.

The dischargers 26A and 26B are formed of a conductive matter, has an elongated shape, and are hollow inside. The hollow portions serve as containers configured to contain starting solutions 32A and 32B. On the respective sides of the dischargers 26A and 26B facing the base sheet 10b, discharge outlets are provided at fixed intervals in a regular arrangement. The starting solutions 32A and 32B are supplied from starting solution tanks 34A and 34B into the hollows of the dischargers 26A and 26B by pressure produced by pumps 33A and 33B which communicate with the hollow portions of the dischargers 26A and 26B. Then, the starting solutions 32A and 32B are discharged from the plurality of discharge outlets toward the primary surface of the base sheet 10b, by pressure produced by the pumps 33A and 33B. The starting solutions discharged cause an electrostatic burst and produce nanofibers, while being electrostatically charged and moving in a space between the dischargers 26A and 26B and the second conveyors 28A and 28B. The nanofibers produced are attracted to the primary surface of the base sheet 10b by an electrostatic attractive force, and are deposited thereon, thereby to form porous layers (non-woven fabrics) comprising the nanofibers.

On the most upstream side of the second conveyor 28A, a squeegee 35 in contact with the primary surface of the base sheet 10b may be provided. The squeegee 35 enables removal of roughness and wrinkles on the primary surface of the base sheet 10b before deposition of the nanofibers thereon. This allows the base sheet 10b to be attached to the surface of the belt part of the second conveyor 28A. Therefore, the nanofibers are uniformly deposited on the primary surface of the base sheet 10b, without becoming unevenly distributed. Thus, the respective surfaces of the porous layers formed become flat and the respective thicknesses thereof are likely to be uniform.

Figure 4:
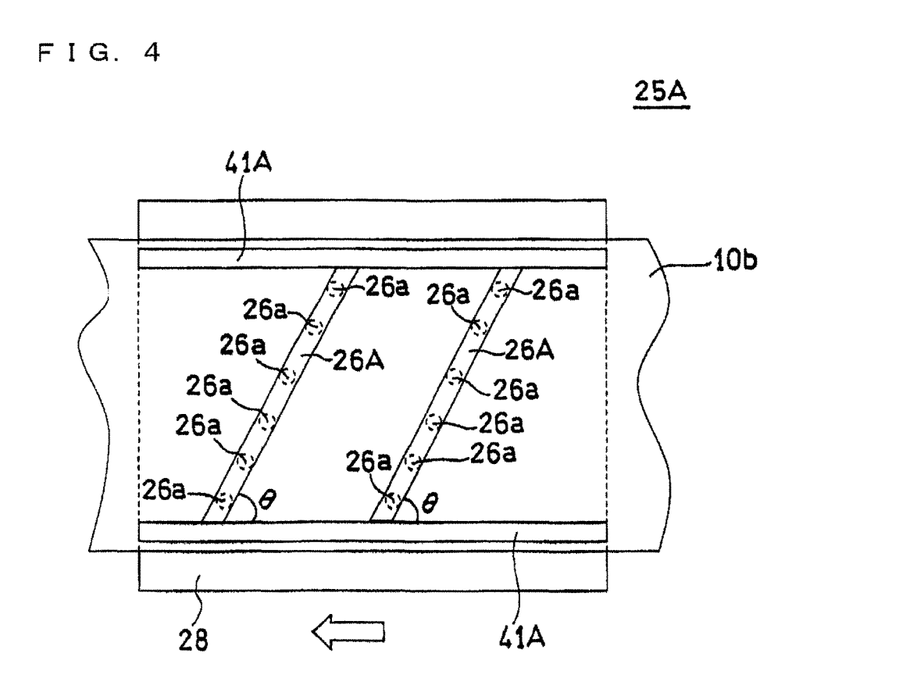
FIG. 4 is a top view of the configuration of an example of an electrostatic spinning unit.

FIG. 4 is a schematic top view of the configuration of the first electrostatic spinning unit 25A. Note that the configuration of the second electrostatic spinning unit 25B (not illustrated) is similar to the configuration in FIG. 4.

In the first electrostatic spinning unit 25A, the discharger 26A is set so as to diagonally cross the direction (direction of outlined arrow in FIG. 4) in which the base sheet 10b is conveyed. Since the discharger 26A is set slanted as above, the second conveyor 28A and the discharger 26A face each other over a wide area and productivity of the porous layer can be increased. The acute angle θ between the discharger 26A and the arrow is not particularly limited, and is preferably about 30° to 60° in terms of improving productivity. The discharger 26A is supported by a second support 42A (42B for the discharger 26B) that extends downward from a first support 41A (41B for the discharger 26B) set at the upper part of the first electrostatic spinning unit 25A and in parallel with the direction in which the base sheet 10b is conveyed, such that the lengthwise direction of the discharger 26A is in parallel with the primary surface of the base sheet 10b.

On the side of the discharger 26A facing the primary surface of the base sheet 10b, a plurality of discharge outlets 26a for the starting solution are provided. Since the discharge outlets 26a are arranged in a regular pattern on the discharger 26A, the amount of the nanofibers deposited on the primary surface of the base sheet 10b can be made uniform over a wide area of the primary surface. The distance between the discharge outlets 26a on the discharger 26A and the base sheet 10b depends on the size of the production system, and may be, for example 100 to 600 mm.

As the foregoing, when the electrostatic spinning mechanism includes: the first electrostatic spinning unit 25A arranged upstream of the production line; and the second electrostatic spinning unit 25B arranged downstream of the production line, it is possible to easily produce nanofibers of different fiber diameters by changing the conditions for nanofiber production at each of the electrostatic spinning units. Therefore, if the fiber diameter of the second nanofibers produced by the second electrostatic spinning unit is intentionally made smaller than the fiber diameter of the first nanofibers produced by the first electrostatic spinning unit, it is possible to obtain the desired membrane for an in vitro diagnostic tool.

The number of the porous layers is not particularly limited as long as the specific surface area of the uppermost porous layer is controlled to be sufficiently large. Therefore, three or more of the porous layers may be formed. In that case, the uppermost porous layer corresponds to the second porous layer, the porous layer therebelow corresponds to the first porous layer, and the porous layer further below can be seen as a part of the base sheet.

The stacked body including the base sheet 10b, the first porous layer 10a, and the second porous layer 10c (i.e., the membrane for an in vitro diagnostic tool) conveyed from the second electrostatic spinning unit 25B is collected by a collecting machine 37 arranged further downstream, via a conveying roller 36. The collecting machine 37 has therein a collecting reel 38 configured to reel in the membrane conveyed thereto. The collecting reel 38 is rotationally driven by a motor 39.

The electrostatic spinning mechanism configured to form the first porous layer and the second porous layer is not particularly limited, as long as it is capable of producing nanofibers from the starting solution by electrostatic force in a predetermined space for nanofiber formation and then depositing the produced nanofibers on the primary surface of the base sheet 10b. For example, the section of the discharger taken perpendicular to its lengthwise direction may have a shape that gradually tapers downwards (V-shaped nozzle). Moreover, the discharger may be a rotating body. Specifically, the discharger may be formed to have a hollow in a manner similar to a tube in a bicycle tire, and the starting solution may be contained in the hollow. If a plurality of discharge outlets are provided along the external surface of the hollow discharger and the annular body is rotated with its center as the axis, the starting solution can be discharged from the discharge outlets by centrifugal force. In that case, if the direction of the starting solution moving in the space is controlled with, for example, a blast of air, the nanofibers can be deposited on a predetermined collector.

Next, a description will be given of a process of causing a reagent configured to react with the suspected substance in the test solution, to be carried in at least a part of the second porous layer in the membrane for an in vitro diagnostic tool.

A method for causing the reagent to be carried in a predetermined region (e.g., region corresponding to a first reagent holding portion or a second reagent holding portion of the second porous layer) is not particularly limited. For example, an aqueous solution of the reagent is prepared and a moderate amount of the aqueous solution is dropped to an open surface of the second porous layer, followed by drying, to cause the reagent to be carried in the predetermined region. The reagent may spread, not only in the second porous layer, but also in the first porous layer and be carried therein.

When the reagent is to be prevented from dissolving into the test solution, that is, when the reagent is to be firmly fixed onto the nanofibers, it is effective, for example, to apply an aqueous solution of the reagent (antibody solution) to the second porous layer and then dry the resultant completely, or to keep the amount of a surfactant to a minimum when used to impart hydrophilicity to the second porous layer.

To lower the polarity of the antibody solution, 1 to 10 mass % of alcohol (e.g., methanol, ethanol, propanol) is preferably added to the antibody solution. Moreover, a phosphate buffer solution is preferably added to the antibody solution to adjust the pH of the antibody solution to around 7.4.

Examples of the antibody useable as the reagent include: antibody against influenza viruses as mentioned above; antibody against proteins in bodily fluid; and antibody against hormones in bodily fluid. These antibodies can be artificially produced. For example, when a test subject such as a mouse or rabbit is sensitized to an antigen, i.e., a protein such as albumen or a hormone such as hCG or LH, cells that produce an antibody against the antigen are obtained. As necessary, a compound such as polyethylene glycol that accelerates an agglutination reaction between the antigen and the antibody may also be included in the reagent holding portion.

In the foregoing, a description was given of the in vitro diagnostic tool and the membrane therefor of the present invention, by mainly referring to examples using immunochromatography. The present invention can be applied to various in vitro diagnostic tests which include steps of dropping a test solution containing a suspected substance to a porous layer, making the test solution flow in the porous layer, and then making the test solution react with a reagent.

INDUSTRIAL APPLICABILITY

The present invention can be applied to various tools (e.g., biosensor) by which an in vitro diagnostic test such as an immunochromatographic test is conducted. Porous layers of different fiber diameters are produced by electrostatic spinning and stacked for use as a main component in the in vitro diagnostic tool, thereby enabling an analysis required of an in vitro diagnostic test to be conducted with quickness and high accuracy.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

EXPLANATION OF REFERENCE NUMERALS 100 in vitro diagnostic tool
10 membrane for in vitro diagnostic tool
10a first porous layer
10b base sheet
10c second porous layer
11 test solution inlet portion
12 first reagent holding portion
12a labeling reagent
13 second reagent holding portion
13a detecting reagent
14 solution absorbing portion
15 test solution
15a suspected substance (antigen)
15b conjugate
200 production system
20 base sheet feeding machine
21 first conveyor
22 feeding reel
24 motor
25A first electrostatic spinning unit
25B second electrostatic spinning unit
26A, 26B discharger
26a discharge outlet
28A, 28B second conveyor
29A, 29B voltage applying device
30A, 30B counter electrode
32A, 32B starting solution
33A, 33B pump
34A, 34B starting solution tank
35 squeegee
36 conveying roller
37 collecting machine
38 collecting reel
39 motor
41A, 41B first support
42A, 42B second support

The invention claimed is:

1. An in vitro diagnostic tool configured to quantitatively or qualitatively detect a suspected substance in a test solution, the tool comprising:
a first porous layer having a first surface and a second surface;
a second porous layer bonded to the second surface; and
a labeling reagent configured to react with the suspected substance and carried in at least a part of the second porous layer; and a detecting reagent configured to immobilize a conjugate of the labeling reagent and the suspected substance,
the second porous layer having: a first reagent holding portion; and second reagent holding portion disposed away from the first reagent holding portion,
the first reagent holding portion configured to carry the labeling reagent,
the second reagent holding portion configured to carry the detecting reagent,
the first porous layer having a matrix structure of first nanofibers,
the second porous layer having a matrix structure of second nanofibers, and
a fiber diameter of the second nanofibers being smaller than a fiber diameter of the first nanofibers.

2. The in vitro diagnostic tool in accordance with claim 1, wherein a rate at which the test solution flows in the first porous layer in a planar direction of the first porous layer is different from a rate at which the test solution flows in the second porous layer in a planar direction of the second porous layer.

3. The in vitro diagnostic tool in accordance with claim 2, wherein the rate at which the test solution flows in the first porous layer in the planar direction of the first porous layer is greater than the rate at which the test solution flows in the second porous layer in the planar direction of the second porous layer.

4. The in vitro diagnostic tool in accordance with claim 1, further comprising a base sheet bonded to the first surface.

5. The in vitro diagnostic tool in accordance with claim 1, wherein the first nanofibers and the second nanofibers are formed by electrostatic spinning.

6. The in vitro diagnostic tool in accordance with claim 1, wherein the second porous layer has a suspected substance inlet portion, the first reagent holding portion being disposed away from the suspected substance inlet portion.

7. A membrane for an in vitro diagnostic tool configured to quantitatively or qualitatively detect a suspected substance in a test solution, the membrane comprising:
a first porous layer having a first surface and a second surface,
and
a second porous layer bonded to the second surface,
the first porous layer having a matrix structure of first nanofibers,
the second porous layer having a matrix structure of second nanofibers, and
a fiber diameter of the second nanofibers being smaller than a fiber diameter of the first nanofibers.

8. The membrane for an in vitro diagnostic tool in accordance with claim 7, wherein a rate at which the test solution flows in the first porous layer in a planar direction of the first porous layer is different from a rate at which the test solution flows in the second porous layer in a planar direction of the second porous layer.

9. The membrane for an in vitro diagnostic tool in accordance with claim 8, wherein the rate at which the test solution flows in the first porous layer in the planar direction of the first porous layer is greater than the rate at which the test solution flows in the second porous layer in the planar direction of the second porous layer.

10. The membrane for an in vitro diagnostic tool in accordance with claim 7, further comprising a base sheet bonded to the first surface.

11. The membrane for an in vitro diagnostic tool in accordance with claim 7, wherein the first nanofibers and the second nanofibers are formed by electrostatic spinning.

12. A production method of an in vitro diagnostic tool, the method comprising:
preparing a base sheet, forming a first porous layer by depositing first nanofibers on one surface of the base sheet by electrostatic spinning, forming a second porous layer by depositing second nanofibers on a surface of the first porous layer not in contact with the base sheet, a fiber diameter of the second nanofibers being smaller than a fiber diameter of the first nanofibers, and causing a labeling reagent configured to react with a suspected substance in a test solution and a detecting reagent configured to immobilize a conjugate of the labeling reagent and the suspected substance, to be carried in at least a part of the second porous layer, the second porous layer having: a first reagent holding portion; and a second reagent holding portion disposed away from the first reagent holding portion, the first reagent holding portion configured to carry the labeling reagent, and the second reagent holding portion configured to carry the detecting reagent.

13. The production method of an in vitro diagnostic tool in accordance with claim 12, wherein the second porous layer has a suspected substance inlet portion, the first reagent holding portion being disposed away from the suspected substance inlet portion.

14. A production method of the membrane for an in vitro diagnostic tool, the method comprising:

preparing a base sheet, forming a first porous layer by depositing first nanofibers on one surface of the base sheet by electrostatic spinning, and forming a second porous layer by depositing second nanofibers on a surface of the first porous layer not in contact with the base sheet, a fiber diameter of the second nanofibers being smaller than a fiber diameter of the first nanofibers.

* * * * *